United States Patent [19]

Kamachi et al.

[11] Patent Number: 4,474,954
[45] Date of Patent: Oct. 2, 1984

[54] INTERMEDIATES FOR CEPHALOSPORIN DERIVATIVES

[75] Inventors: Hajime Kamachi, Ciba; Jun Okumura, Yokohama; Takayuki Naito, Kawasaki; Masahisa Oka, Yokoyama, all of Japan

[73] Assignee: Bristol-Myers Company, New York, N.Y.

[21] Appl. No.: 447,064

[22] Filed: Dec. 6, 1982

Related U.S. Application Data

[62] Division of Ser. No. 328,331, Dec. 7, 1981, Pat. No. 4,394,503.

[51] Int. Cl.$^3$ ................ C07D 501/38; A61K 31/545
[52] U.S. Cl. ....................................... 544/24; 544/25; 544/21; 424/246
[58] Field of Search .................. 544/25, 26, 24; 424/246

[56]         References Cited
    U.S. PATENT DOCUMENTS 4,237,128 12/1980 Cimarusti et al. ............ 424/246
 4,258,041  3/1981 O'Callaghan et al. ......... 424/246
 4,278,793  7/1981 Dürckheimer et al. .......... 544/25

FOREIGN PATENT DOCUMENTS 1399086 6/1975 United Kingdom .
 2063871 6/1981 United Kingdom .
 2064513 6/1981 United Kingdom .

Primary Examiner—Nicholas S. Rizzo
Attorney, Agent, or Firm—Richard R. Lloyd

[57]         ABSTRACT

Potent antibacterial agents of the formula

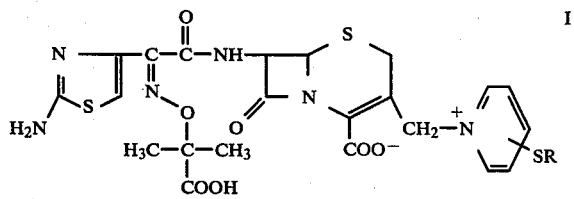

wherein R is methyl, ethyl or isopropyl, and their pharmaceutically acceptable salts, physiologically hydrolyzable esters and solvates, and processes for their preparation, are described.

4 Claims, No Drawings

INTERMEDIATES FOR CEPHALOSPORIN DERIVATIVES

CROSS-REFERENCE TO RELATED APPLICATION

This application is a divisional of our prior, co-pending application Ser. No. 328,331, filed Dec. 7, 1981, now U.S. Pat. No. 4,394,503.

SUMMARY OF THE INVENTION

Cephalosporin derivatives of the formula

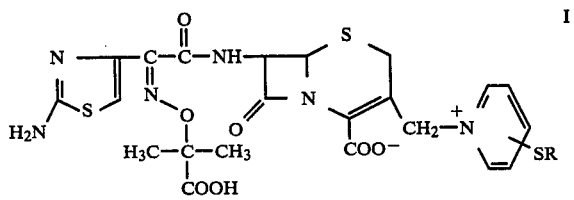

wherein R is methyl, ethyl or isopropyl, and their pharmaceutically acceptable salts, physiologically hydrolyzable esters and solvates (including particularly the hydrates) are potent antibacterial agents. Processes for their preparation are also described.

PRIOR ART

U.K. Pat. No. 1,399,086 contains a generic disclosure encompassing a vast number of cephalosporins of the formula

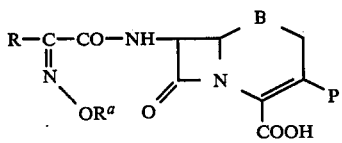

wherein R is hydrogen or an organic group, $R^a$ is an etherifying monovalent organic group linked to the oxygen through a carbon atom, B is

or

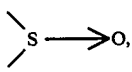

and P is an organic group. Thus, the compounds of this invention are literally included within its generic disclosure. However, the 2-aminothiazol-4-yl group is not exemplified (or named) as an R substituent and the 2-carboxyprop-2-yl group is not exemplified (or named) as an $R^a$ substituent. Pyridiniummethyl and 4-carbamoylpyridiniummethyl are exemplified as P substituents, but methylthio-substituted pyridiniummethyl is not exemplified. U.S. Pat. No. 3,971,778, and its divisional U.S. Pat. No. 4,024,137, are related patents having substantially identical disclosures.

U.S. Pat. No. 4,278,793 contains a generic disclosure encompassing a vast number of cephalosporins of the formula

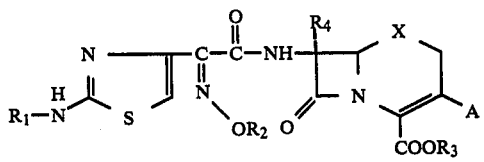

in which $R_1$ is hydrogen, an optionally substituted alkyl, acyl, arylsulfonyl or alkylsulfonyl group, or an aminoprotective group which is known from peptide chemistry; $R_2$ is hydrogen or an optionally substituted alkyl, alkenyl, alkinyl, cycloalkyl, aralkyl, acyl, aryl, arylsulfonyl, alkylsulfonyl or heterocyclic group; $R_3$ is hydrogen, an ester group or a cation; $R_4$ is hydrogen, a lower alkoxy group or a group which can be converted to this; X is sulfur, oxygen, —$CH_2$— or —NH—; and A is hydrogen, an optionally substituted alkoxy or alkenyloxy group, halogen, or a group —$CH_2Y$ in which Y is hydrogen, halogen or the radical of a nucleophilic compound; and in which the $R_2O$ group is in the syn position. Thus, the compounds of this invention are literally included within its generic disclosure. This generic disclosure is followed by over a column of exclusions to the generic disclosure and then by approximately 20 columns of definitions of the various substituent groups. The 2-carboxyprop-2-yl group is not exemplified (or named) as an $R_2$ substituent and no methylthio substituted pyridiniumethyl groups are exemplified or named as A substituents. Published U.K. Patent Application No. 2,028,305 A, although apparently not formally related, contains the same broad generic disclosure (without the exclusions). However, it exemplifies A only as hydrogen and $R_2$ only as methyl and ethyl.

U.S. Pat. No. 4,258,041 discloses cephalosporins of the formula

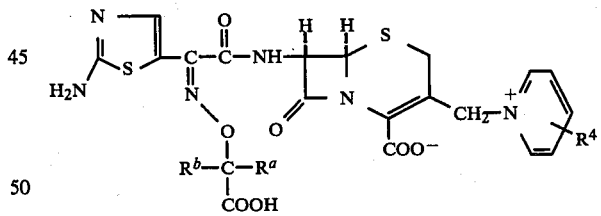

wherein $R^a$ and $R^b$ are the same or different and are $C_{1-4}$ alkyl group, or $R^a$ and $R^b$, taken together with the carbon atom to which they are attached, form a $C_{3-7}$ cycloalkylidiene group; and $R^4$ is hydrogen or a 3- or 4-carbamoyl group; and nontoxic salts and metabolically labile esters thereof. $R^a$ and $R^b$ are exemplified as both being methyl, thus giving the 2-carboxyprop-2-oxyimino moiety, but $R^4$ cannot be methylthio. Published U.K. Patent Application No. 2,025,398 A is concordant and has a substantially identical disclosure. Published U.K. Patent Application No. 2,058,791 A is similar to U.K. No. 2,025,398 A, but specifically provides that $R^a$ and $R^b$ cannot both be methyl when $R^4$ is hydrogen.

U.S. Pat. No. 4,237,128 discloses cephalosporin derivative 1-oxides of the formula

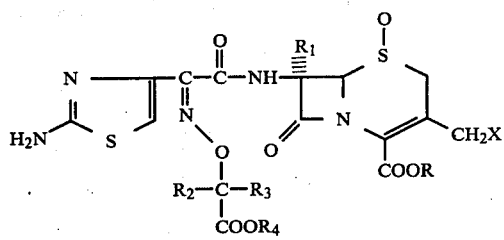

wherein R is hydrogen, sodium, potassium or certain ester groups; $R_1$ is in the α-configuration and is hydrogen or methoxy; $R_2$ and $R_3$ are independently selected from methyl, ethyl, isopropyl and n-propyl; $R_4$ is hydrogen, sodium, potassium or certain ester groups; and X is lower alkanoyloxy, carbamoyloxy,

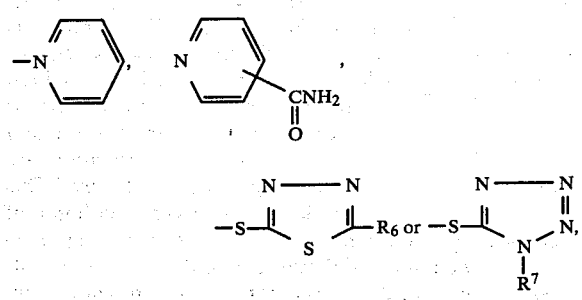

$R^6$ is hydrogen or lower alkyl; $R_7$ is hydrogen, lower alkyl, $-(CH_2)_nCOOR_8$, $-(CH_2)_nSO_3R_8$ or $-(CH_2)_nN(lower\ alkyl)_2$; $R_8$ is hydrogen, sodium or potassium; and n is 1-4. The compounds in which R, $R_1$ and $R_4$ each are hydrogen, $R_2$ and $R_3$ each are methyl and X is pyridinium or carbamoyl substituted pyridinium are exemplified. Published U.K. Patent Application No. 2,049,675 and Belgian Pat. No. 882,758 are concordant thereto.

Published U.K. Patent Application No. 2,064,513 A discloses the bishydrochloride of ceftazidime (GR 20263) of the formula

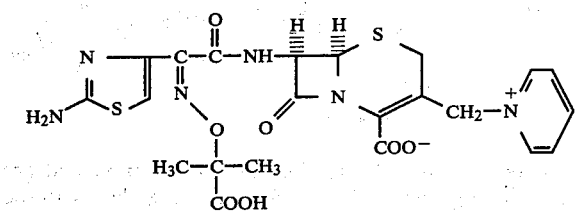

which has a well defined crystalline structure and good storage stability. Belgian Pat. No. 885,488 is concordant thereto.

Published U.K. Patent Application No. 2,063,871 discloses the pentahydrate of ceftazidime, which has a well defined crystalline structure and good storage stability. Beligan Pat. No. 885,489 is concordant thereto.

COMPLETE DISCLOSURE

This invention relates to cephalosporin compounds having the formula

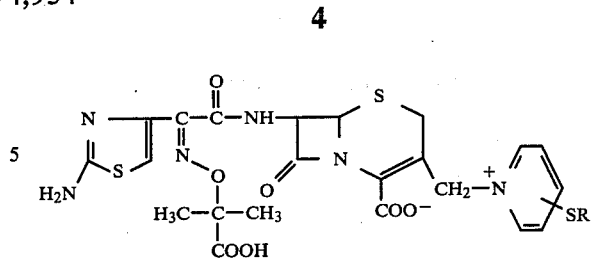

wherein R is methyl, ethyl or isopropyl, and the pharmaceutically acceptable salts, physiologically hydrolyzable esters and solvates (including particularly the hydrates) thereof. The preferred compounds are those in which R is methyl and it is particularly preferred that —SR is a methylthio group in the 4-position of the pyridinium moiety. In another aspect, this invention relates to processes for the preparation of the compounds of Formula I.

As shown in the structural formula, the compounds of Formula I have the "syn" or "Z" configuration with respect to the 2-carboxyprop-2-oxyimino group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers. Included within the scope of the invention are the alternative zwitterionic forms of the compounds of Formula I in which the carboxyl group in the 4-position is protonated and the carboxyl group in the 7-side chain is deprotonated. Also included are the tautomeric forms of the compounds of Formula I, e.g. the 2-iminothiazolin-4-yl form of the 2-aminothiazol-4-yl moiety.

The pharmaceutically acceptable salts of the compounds of Formula I include the inorganic base salts such as the alkali metal salts (e.g. the sodium and potassium salts) and the alkaline earth metal salts (e.g. the calcium salts), ammonium salts, organic base salts (e.g. with triethylamine, procaine, phenethylbenzylamine, dibenzylethylenediamine and other organic bases which have been used in the penicillin and cephalosporin art), and the acid addition salts (e.g. the salts with hydrochloric, hydrobromic, formic, nitric, sulfuric, methanesulfonic, phosphoric, acetic or trifluoroacetic acid). The physiologically hydrolyzable esters (which may be formed with either or both of the carboxyl groups of the compounds of Formula I) include the acyloxyalkyl esters, e.g. (lower)alkanoly(lower)alkyl esters such as acetoxymethyl, acetoxyethyl, pivaloyloxymethyl and the like.

The compounds of Formula I exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage froms the compositions will preferably contain from about 50 to about 1500 mg of the active ingredient of Formula I. The dosage for adult human treatment will perferably be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses may be required in the case of Pseudomonas infections.

In another aspect, this invention relates to processes for the preparation of the compounds of Formula I. There are two basic procedures for converting a readily available starting cephalosporin to another cephalosporin having different substituents on the 7- and 3-positions. One may first remove the 7-substituent and replace it with the desired 7-substituent, and then insert the desired 3-substituent. Alternatively, one may first insert the desired 3-substituent and subsequently exchange the 7-substituent. Prior art processes for the preparation of compounds closely related to those of Formula I (e.g. ceftazidime) have, in general, given poor yields of product via any of several variations of the two basic procedures set forth above. One common process for the preparation of ceftazidime is the reaction of 7-[(Z)-2-(2-aminothiazol-4-yl)-2-(2-carboxyprop-2-oxyimino)acetamidocephalosporanic] acid having the formula

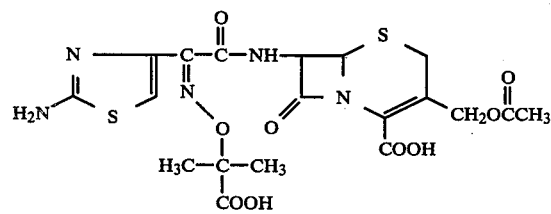
V with pyridine to effect nucleophilic replacment of the acetoxy group by the pyridinium moiety and produce ceftazidime having the formula

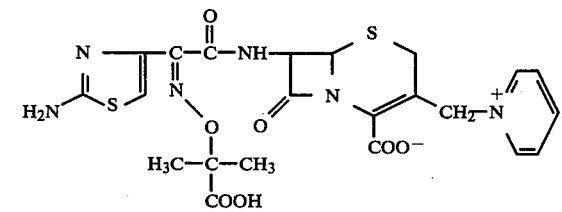

When preparing the compound of Formula I in which —SR is a 4-methylthio group (Ic) by reacting V in an analogous manner with 4-methylthiopyridine, this single step reaction produced compound Ic in only 5% yield (see Example 2). Published U.K. Application No. 2,025,398, in Example 1, Steps (a) and (b), describes the preparation of compound V in a 38.8% yield from 7-aminocephalosporanic acid. Given the 5% yield of compound Ic from compound V, the yield of compound Ic from 7-aminocephalosporanic acid via this procedure would be about 1.9%. Taking into account the preparation of 7-aminocephalosporanic acid by the deacylation of a starting cephalosporin, the overall yield of compound Ic by such a process would be about 1%.

Four novel, multi-step reaction schemes for the preparation of the compounds of Formula I are given below, each illustrating the preparation of the most preferred compound Ic from benzhydryl 3-hydroxymethyl-7-phenylacetamido-3-cephem-4-carboxylate (VI). The following abbreviations are used in these reaction schemes.

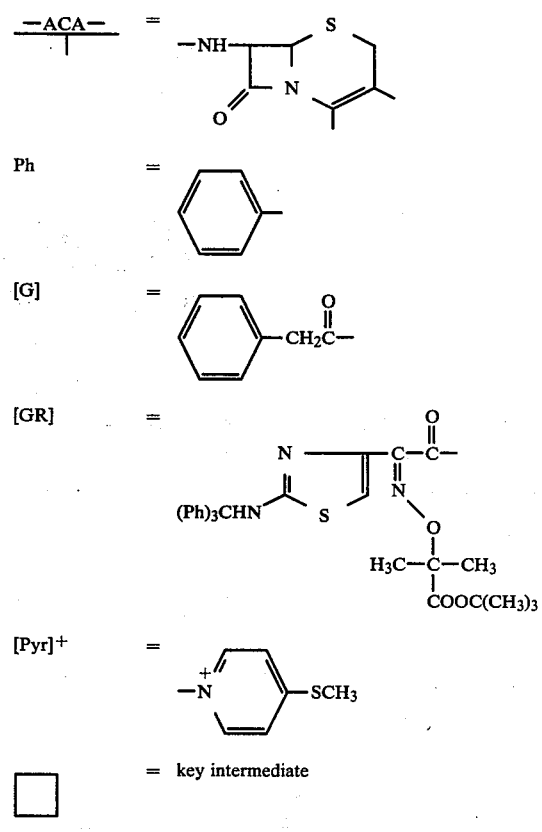

☐ = key intermediate

REACTION SCHEMES A-1 AND A-2

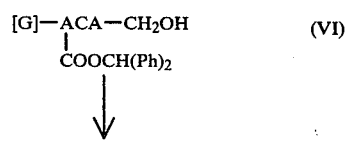
(VI)

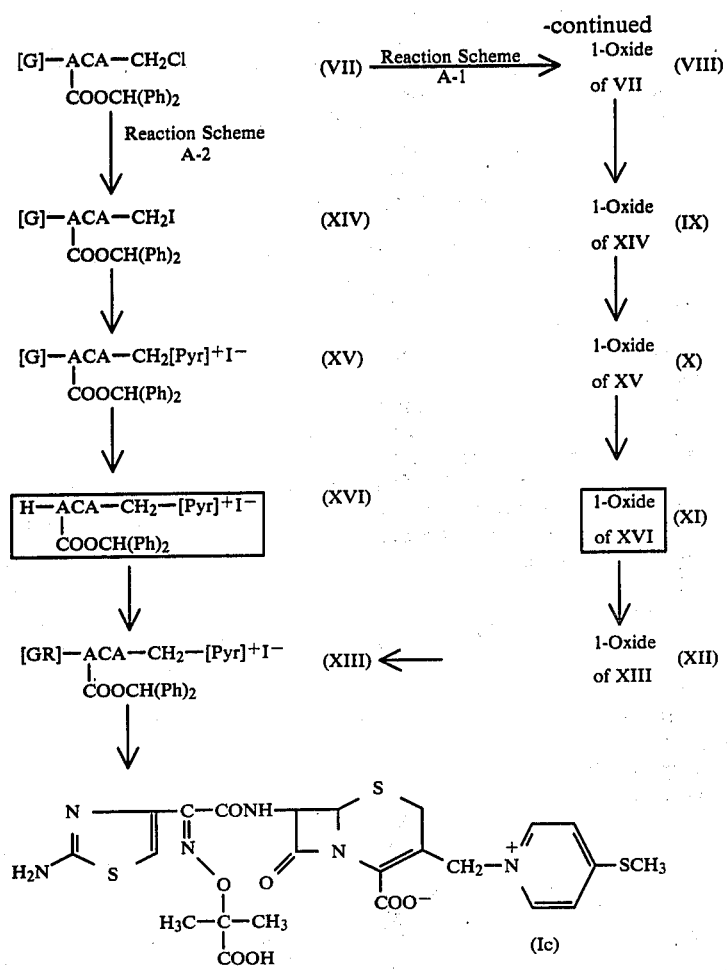
REACTION SCHEMES B-1 AND B-2
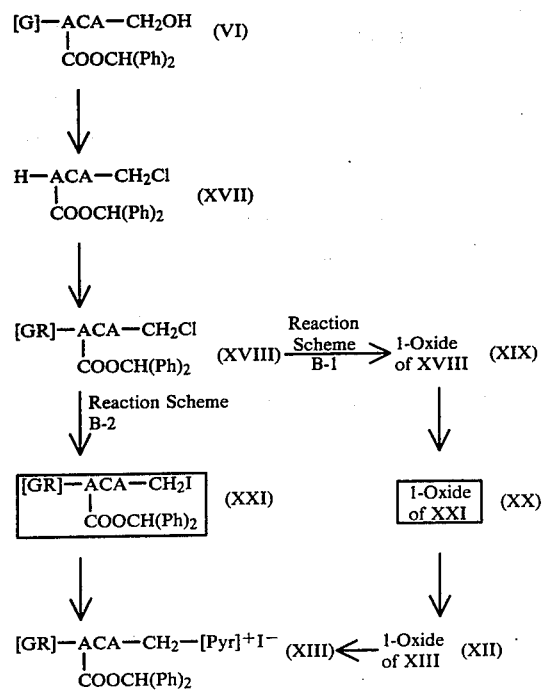

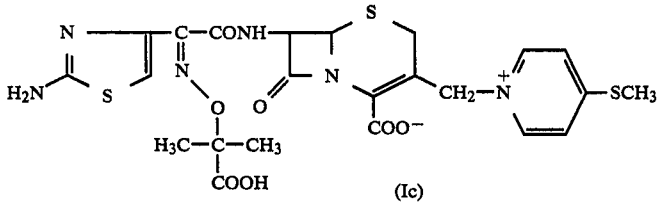

(Ic)

Reaction Schemes A-1 and A-2 involve the conversion of the 3-hydroxymethyl group to the 3-(4-methylthiopyridinium)methyl moiety, followed by conversion of the 7-phenylacetamido side chain to the desired 7-[(Z)-2-(2-aminothiazol-4-yl)-2-(2-carboxyprop-2-oxyimino)acetamido] side chain. Reaction Schemes A-1 and A-2 differ only in that Scheme A-1 involves conversion of the first intermediate (VII) to its 1-oxide, performing all subsequent reaction steps on the 1-oxide, and reduction of the 1-oxide just before removal of all protecting groups. Even though Reaction Scheme A-1 involves two additional steps over Reaction Scheme A-2, it provides an overall yield from compound VI which is much higher than that obtained via Reaction Scheme A-2. Reaction Schemes B-1 and B-2 involve the conversion of the 7-phenylacetamido side chain to the desired 7-[(Z)-2-(2-aminothiazol-4-yl)-2-(2-carboxyprop-2-oxyimino)acetamido] side chain, followed by conversion of the 3-hydroxymethyl substituent to the 3-(4-methylthiopyridinium)methyl moiety. Again, Reaction Schemes B-1 and B-2 differ in that most of the steps of Scheme B-1 are carried out on the 1-oxide. Overall yields of compound Ic from compound VI via Reaction Schemes B-1 and B-2 are only about one-tenth as high as are obtained via Reaction Scheme A-1. Reaction Schemes A-1 and A-2 are the preferred processes, and Reaction Scheme A-1 is the most preferred process.

As shown above, Reaction Schemes A-1, A-2, B-1 and B-2 each utilize compound VI as starting material. It will be appreciated by those skilled in the art, however, that various other starting materials may be used. Thus, in each reaction scheme there is a key intermediate (shown enclosed by a box) from which the final products are prepared. These key intermediates may themselves be prepared from any convenient cephalosporin starting material by any conventional procedures.

The present invention provides a process for the preparation of compounds of the formula

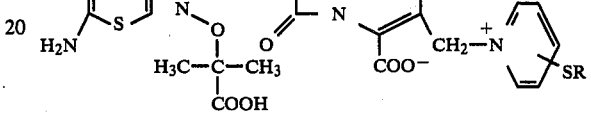

I in which R is methyl, ethyl or isopropyl, or a pharmaceutically acceptable salt, physiologically hydrolyzable ester or solvate thereof, which comprises acylating a compound of the formula

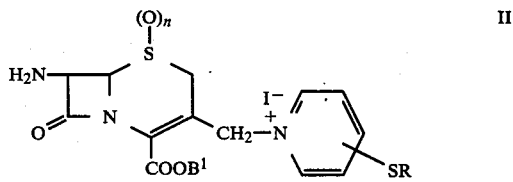

II or an N-silyl derivative thereof, wherein R is as defined above, n is zero or 1 and $B^1$ is hydrogen or a carboxyl-protecting group, with an acylating derivative of an acid of the formula

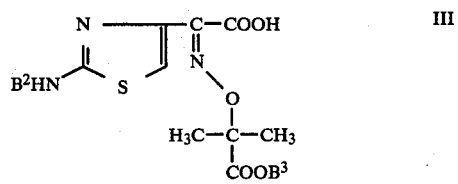

III wherein $B^2$ is an amino-protecting group and $B^3$ is a carboxyl-protecting group, to produce the compound of the formula

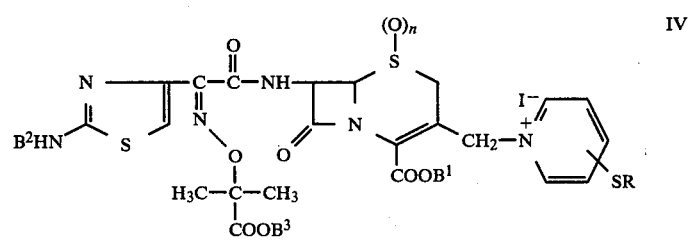

IV and, if n is 1, reducing the 1-oxide moiety by conventional means, and removing all protecting groups by conventional means.

The acylating derivatives of the acid of Formula III include the acid halides (and particularly the acid chloride), mixed acid anhydrides (such as the acid anhydrides formed with pivalic acid or a haloformate such as ethyl chloroformate), and activated esters (such as may be formed with N-hydroxybenztriazole in the presence of a condensing agent such as dicyclohexylcarbodiimide). The acylation may also be effected by used of the free acid of Formula III in the presence of a condensing agent such as dicyclohexylcarbodiimide, carbonyldiimidazole or an isoxazolium salt. As used herein and in the claims, the term "acylating derivative" of the acid of Formula III includes the free acid itself in the presence of a condensing agent such as described above. The preferred acylating derivative of the acid of Formula III is the acid chloride, preferably used in the presence of an acid binding agent (and particularly a tertiary amine acid binding agent such as triethylamine, dimethylaniline or pyridine).

When the acylation is conducted with an acid halide it is possible to utilize an aqueous reaction medium, but a non-aqueous medium is preferred. When acid anhydrides, activated esters, or the free acid in the presence of a condensing agent, are used for the acylation, the reaction medium should be non-aqueous. Particularly preferred solvents for the acylation reaction are halogenated hydrocarbons such as methylene chloride and chloroform, but tertiary amides such as dimethylacetamide or dimethylformamide may be utilized, as well as other conventional solvents such as tetrahydrofuran, acetonitrile and the like.

The acylation reaction may be conducted at a temperature of from about $-50°$ C. to about $+50°$ C. However, it is preferably conducted at or below room temperature and most preferably from about $-30°$ C. to about $0°$ C. It is usually preferred to acylate the compound of Formula II with about a stoichiometric amount of the acylating agent of Formula III, although a small excess (e.g. 5–25%) of the acylating agent may be utilized.

It is preferable that the compound of Formula II be acylated in the form of its N-silyl derivative (when utilizing a non-aqueous reaction medium). This is conveniently done in situ by simply adding a suitable silylating agent (e.g. N,O-bistrimethylsilylacetamide) to the solution of compound II prior to the addition of the acylating agent of Formula III. We prefer to utilize about 3 moles of silylating agent per mole of compound II although this is not critical. The silyl compound is readily removed after acylation by the addition of water.

Carboxyl-protecting groups suitable for use as $B^1$ and $B^3$ in the above reaction are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl; and other carboxyl-protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl. Amino-protecting groups which are readily removed by treatment with acid, e.g. the trityl group, are preferred.

When utilizing Reaction Schemes A-1 or B-1, the 1-oxide is prepared by known procedures such as oxidation with m-chloroperbenzoic acid, peracetic acid, etc. The 1-oxide subsequently may be reduced by known procedures, e.g. reduction of the corresponding alkoxysulfonium salt with iodide ion in an aqueous medium. The alkoxysulfonium salt itself is readily prepared by treatment of the 1-oxide with, for example, acetyl chloride.

This invention also provides a process for the preparation of compounds of the formula

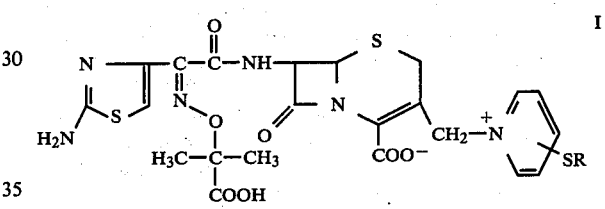

in which R is methyl, ethyl or isopropyl, or a pharmaceutically acceptable salt, physiologically hydrolyzable ester or solvate thereof, which comprises reacting a compound of the formula

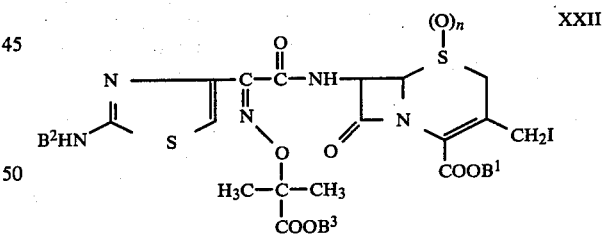

wherein n is zero or 1, $B^1$ and $B^3$ are each hydrogen or a carboxyl-protecting group and $B^2$ is hydrogen or an amino-protecting group, with a substituted pyridine of the formula

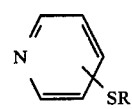

XXIII wherein R is as defined above, to produce the compound of the formula

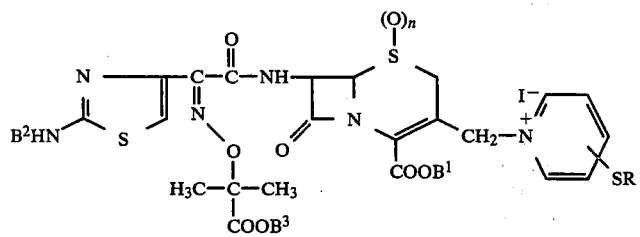

IV and, if n is 1, reducing the 1-oxide moiety by conventional means, and removing all protecting groups.

The reaction of compounds XXII and XXIII is carried out in a non-aqueous organic solvent such as described above; methylene chloride is a preferred solvent. The reaction is conveniently carried out at a temperature of from about −10° C. to about 50° C.; we normally prefer to conduct the reaction at room temperature. At least one mole of the substituted pyridine compound XXIII should be utilized per mole of compound XXII and an excess is preferred. We normally prefer to use about 100% excess of compound XXIII.

The acylating acid of the Formula III, including carboxy- and amino-protected derivatives thereof, is known in the art. The preparation of (Z)-2-(2-t-butoxycarbonylprop-2-oxyimino)-2-(2-tritylaminothiazol-4-yl)acetic acid is described, for example, in U.S. Pat. No. 4,258,041 and U.K. Patent Application No. 2,025,398.

The alkylthiopyridines of Formula XXIII may be prepared by reaction of the corresponding mercaptopyridine with the appropriate alkyl iodide according to published procedures [see J. Chem. Soc., 873 (1939) and J. Chem. Soc., 2384 (1959)]. The synthesis of 4-isopropylthiopyridine from 4-mercaptopyridine and isopropyl iodide is given below in Preparation No. 2. The 2- and 4-mercaptopyridines are commercially available, and 3-mercaptopyridine may be prepared according to the general procedure described in United Kingdom Pat. No. 637,130.

The minimum inhibitory concentrations (MIC's) of the compounds of this invention and ceftazidime were determined by a two-fold agar dilution method, using Steer's multi-inoculator on Mueller-Hinton agar plates, against 32 test organisms consisting of six groups. Table 1 shows the in vitro activity of some of the preferred compounds in terms of the geometric mean of the MIC values calculated for the six test organism groups. Table 2 shows the MIC values for some of the compounds against representative strains selected from the 32 test organisms.

Table 3 shows the geometric mean MIC's of a preferred compound of this invention and ceftazidime against 29 strains of six groups of Streptococcus, Neisseria and Haemophilis species.

Table 4 shows the geometric mean MIC's of two of the preferred compounds of this invention and ceftazidime against 12 strains of anaerobic bacteria in four groups.

The in vivo activities of some of the preferred compounds of this invention and ceftazidime were determined by experimental infections in mice challenged intraperitoneally with various pathogenic bacteria. The test compounds were administered intramuscularly immediately after the bacterial challenge. Groups of five mice were used for each dose level and the animals were observed for five days to determine the median protective dose ($PD_{50}$) by the log-probit method. The results are shown in Table 5.

The absorption of the compound of Example 2 and of ceftazidime were determined in mice following a single intramuscular injection of the test compound at either 20 mg/kg or 10 mg/kg. Blood samples were collected from the orbital sinuses into heparinized capillary tubes and assayed by the paper disc-agar diffusion method using *E. coli* as the test organism. The half-life values and areas under the curve were determined. The results are shown in Table 6.

TABLE 1

In Vitro Antibacterial Activity in Mueller-Hinton Agar

| Group of Organisms[a] | Number of Strains | Geometric Mean of MIC (mcg/ml) | | | | | |
|---|---|---|---|---|---|---|---|
| | | Compound of Example | | | | | Ceftazidime[b] |
| | | 1 | 2 | 3 | 4 | 5 | |
| Gp-Ia | 5 | 4.7 | 4.7 | 9.5 | 6.3 | 4.7 | 6.3 |
| Gp-Ib | 5 | 12.5 | 6.3 | 12.5 | 12.5 | 12.5 | 12.5 |
| Gn-Ia | 5 | 0.11 | 0.066 | 0.11 | 0.087 | 0.11 | 0.066 |
| Gn-Ib | 6 | 1.1 | 0.89 | 2.0 | 1.3 | 1.0 | 1.6 |
| Gn-II | 5 | 2.8 | 1.5 | 3.2 | 2.1 | 2.4 | 2.7 |
| Gn-III | 6 | 3.5 | 3.1 | 5.6 | 8.8 | 12.5 | 2.0 |

[a]Gp-Ia = Penicillin-sensitive *S. aureus*
Gp-Ib = Penicillin-resistant *S. aureus*
Gn-Ia = Cephalothin-sensitive *E. coli* (2 strains), *Kl. pneumoniae* (1) and *Pr. mirabilis* (2)
Gn-Ib = Cephalothin-resistant *E. coli* (3) and *Kl. pneumoniae* (3)
Gn-II = *Pr. morganii* (1), *Ent. cloacae* (2) and *Ser. marcescens* (2)
Gn-III = *Ps. aeruginosa*
[b]Mean of 3 experiments
Gp = Gram positive
Gn = Gram negative

TABLE 2

Minimum Inhibitory Concentration (mcg/ml)
Against Selected Test Organisms

| Group | Organisms | Resistance Profile* | Compound of Example | | Ceftazidime |
|---|---|---|---|---|---|
| | | | 1 | 2 | |
| Gp-Ia | *S. aureus* Smith | PC-S | 6.3 | 6.3 | 6.3 |
| Gp-Ia | *S. aureus* A9497 | " | 3.1 | 3.1 | 3.1~6.3 |
| Gp-Ib | *S. aureus* BX-1633 | PC-R | 12.5 | 6.3 | 6.3~12.5 |
| | *S. aureus* A15092 | " | 12.5 | 6.3 | 6.3~12.5 |
| Gn-Ia | *E. coli* Juhl | CET-S | 0.2 | 0.1 | 0.1 |
| | *K. pneumoniae* D11 | " | 0.4 | 0.1 | 0.1 |

TABLE 2-continued

Minimum Inhibitory Concentration (mcg/ml)
Against Selected Test Organisms

| Group | Organisms | Resistance Profile* | Compound of Example 1 | Compound of Example 2 | Ceftazidime |
|---|---|---|---|---|---|
| | P. mirabilis A9554 | " | 0.1 | 0.05 | 0.05 |
| Gn-Ib | E. coli A15148 | CET-R | 0.4 | 0.2 | 0.4 |
| | K. pneumoniae A9867 | " | 3.1 | 3.1 | 6.3 |
| Gn-II | P. morganii A9553 | CET-R | 1.6 | 1.6 | 3.1 |
| | E. cloacae A9656 | " | 0.4 | 0.2 | 0.2~0.4 |
| | S. marcescens A20019 | " | 0.2 | 0.4 | 0.1 |
| Gn-III | P. aeruginosa A15150 | CET-R | 1.6 | 1.6 | 0.8 |
| | P. aeruginosa A9843 | " | 3.1 | 1.6 | 1.6 |
| | P. aeruginosa A20717 | " | 12.5 | 6.3 | 6.3 |
| Anaerobe | B. fragilis A20928-1 | CET-S | 6.3 | 3.1 | 3.1 |
| | B. fragilis A21900 | " | 6.3 | 6.3 | 25 |
| | B. fragilis A22021 | CET-R | 25 | 12.5 | 12.5 |
| | B. fragilis A22693 | " | 25 | 12.5 | 12.5 |
| | B. fragilis A22695 | AMP-R | 50 | 50 | 50 |
| | B. fragilis A22533 | " | >100 | >100 | >100 |
| Anaerobe | C. difficile A21675 | CLDM-R | >100 | >100 | >100 |
| | C. perfringens A9635 | " | 25 | 12.5 | 6.3 |
| | P. acnes A21933 | " | 1.6 | 1.6 | 1.6 |

*PC = Penicillin, CET = Cephalothin, AMP = Ampicillin, CLDM = Clindamycin, S = Sensitive, R = Resistant

TABLE 3

In Vitro Activity Against Species of
Streptococcus, Neisseria and Haemophilus

| Organism | Number of Strains | Geometric Mean of MIC (mcg/ml) Compound of Example 2 | Ceftazidime |
|---|---|---|---|
| S. pyogenes | 5 | 0.20 | 0.40 |
| S. pneumoniae | 5 | 0.20 | 0.40 |
| N. gonorrhoeae | 4 | 0.013 | 0.10 |
| N. meningitidus | 5 | 0.013 | 0.10 |
| H. influenzae (AMP-R) | 3 | 0.40 | 0.20 |
| H. influenzae (AMP-S) | 7 | 0.10 | 0.055 |

TABLE 4

In Vitro Antianaerobic Activity (In GAM Agar)

| Organism | Geometric Mean of MIC (mcg/ml) | | | |
|---|---|---|---|---|
| | Compound of Example 4 | Ceftazidime[a] | Compound of Example 5 | Ceftazidime[b] |
| B. fragilis Group I | 2.5 | 5.3 | 3.2 | 8.9 |
| B. fragilis Group II | 12.5 | 13 | 25 | 16 |
| B. fragilis Group III | 100 | 81 | >100 | >100 |
| Others Group IV | 8.9 | 6.2 | 3.5 | 8.2 |

[a]Mean of 3 experiments
[b]Mean of 2 experiments
Group I: Non-β-lactamase-producing B. fragilis sensitive to ampicillin (3 strains)
Group II: β-Lactamase-producing B. fragilis moderately resistant to ampicillin (3 strains)
Group III: β-Lactamase-producing B. fragilis highly resistant to ampicillin (2 strains)
Group IV: C. difficile, C. perfringens, P. acne and P. anaerobius (1 strain each)

TABLE 5

Therapeutic Efficacy in Experimentally Infected Mice
PD$_{50}$ (mg/kg) i.m.

| Organism | Compound of Example 1 | Compound of Example 2 | Ceftazidime |
|---|---|---|---|
| S. aureus Smith | 6.0 | 5.0 | 10.0 |
| S. aureus BX-1633 | — | 15 | 15 |
| E. coli Juhl | 0.46 | 0.16 | 0.11 |
| P. aeruginosa A9843 | 12 | 12 | 6.0 |
| Pr. mirabilis A9900 | — | 0.63 | 0.90 |
| E. cloacae A9656 | — | 3.5 | 3.5 |

TABLE 6

Blood Levels After Intramuscular Administration to Mice

| Compound | Dose (mg/kg) | Blood Levels (mcg/ml) Minutes After Administration | | | | | | T$_{\frac{1}{2}}$ (minutes) | Area Under Curve (mcg · hour/ml) |
|---|---|---|---|---|---|---|---|---|---|
| | | 10 | 20 | 30 | 40 | 60 | 90 | | |
| Example 2 | 20 | 12 | 12 | 9.3 | 8.7 | 4.0 | 1.2 | 16 | 10 |
| " | 10 | 4.5 | 5.1 | 3.8 | 3.2 | 1.1 | 0.45 | 18 | 3.7 |
| Ceftazidime | 20 | 18 | 14 | 11 | 7.7 | 2.4 | 0.61 | 14 | 10 |
| " | 10 | 8.0 | 7.8 | 5.5 | 3.9 | 1.8 | 0.40 | 16 | 5.5 |

PREPARATION NO. 1

Benzhydryl
3-Hydroxymethyl-7-phenylacetamido-3-cephem-4-carboxylate (VI)

To a stirred suspension of phosphate buffer (pH 7, 162.5 ml) and wheat bran (20 g, dry) at room temperature was added 7-phenylacetamidocephalosporanic acid sodium salt (5 gm, 12.1 mmole) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 ml) followed by a 0.5M solution of diphenyldiazomethane in methylene chloride (24 ml). The pH was then adjusted to 3.0 with 28% phosphoric acid. After 1 hour the reaction mixture was allowed to rise to 20° C. Heptan (56 ml) was slowly added and the resulting crystalline VI was recovered by filtration. Yield of VI was 3.0 gm (50%).

PREPARATION NO. 2

4-Isopropylthiopyridine

A mixture of 4-mercaptopyridine (555 mg, 5 mmoles) and isopropyl iodide (0.50 ml) in ethanol (5 ml) was heated under reflux for 4 hours and then evaporated under reduced pressure. The residue was dissolved in a small amount of water, made alkaline with aqueous sodium hydroxide and extracted with ethyl acetate. The extract was washed with a small amount of water, dried and evaporated under reduced pressure to give the product as an oil. Yield, 670 mg (88%).

IR: $\nu_{max}^{liq}$ cm$^{-1}$ 1570, 1470, 1400, 885, 690.

UV: $\nu_{max}^{EtOH}$ nm($\epsilon$) 208 (7870), 267 (11750).

NMR: $\delta^{CDCl_3}$ ppm 1.40 (6H, d, 7 Hz, isopropyl), 3.58 (1H, q, 7 Hz, isopropyl), 7.10 (2H, d, 7 Hz, pyridine), 8.40 (2H, d, 7 Hz, pyridine).

EXAMPLE 1

7-[(Z)-2-(2-Aminothiazol-4-yl)-2-(2-carboxyprop-2-oxyimino)acetamido]-3-[(3-methylthiopyridinium)methyl]-3-cephem-4-carboxylate (Ib)

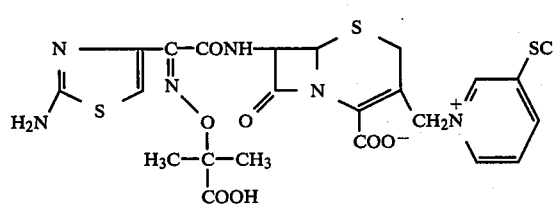

A mixture of the sodium salt of 7-[(Z)-2-(2-aminothiazol-4-yl)-2-(2-carboxyprop-2-oxyimino)acetamido]cephalosporanic acid (V) (571 mg, 1 mmole), potassium thiocyanate (5 g) and 3-methylthiopyridine (125 mg, 1 mmole) in water (1 ml) was adjusted to pH 7 with hydrochloric acid and heated at 75° C. for 90 minutes. The mixture was diluted with acetone (100 ml) to precipitate the crude product, which was collected by filtration and dissolved in a small amount of water. The solution was acidified to pH 2 with dilute hydrochloric acid and filtered to remove insolubles. The filtrate was chromatographed on a column of HP-20 resin (1.3×20 cm) and eluted with water and then with water-methanol (2:1). The fractions containing the desired product were combined and evaporated under reduced pressure, and the aqueous residue was freeze-dried to give the title compound as an amorphous powder. Yield, 65 mg (11%).

ir: $\nu_{max}^{KBr}$ 1770, 1660, 1610, 1390, 1160 cm$^{-1}$.

uv: $\nu_{max}^{pH7Buffer}$ 234 nm ($\epsilon$, 21100), 270 nm ($\epsilon$, 18400).

nmr: $\delta^{D_2O+NaHCO_3}$ ppm 1.50(6H, s, gem-CH$_3$), 2.60(3H, s, SCH$_3$), 5.23(1H, d, 4 Hz, 6-H), 5.80(1H, d, 4 Hz, 7-H), 7.02(1H, s, thiazol 5-H), 7.7–8.8(4H, m, pyridine).

EXAMPLE 2

7-[(Z)-2-(2-Aminothiazol-4-yl)-2-(2-carboxyprop-2-oxyimino)acetamido]-3-[(4-methylthiopyridinium)methyl]-3-cephem-4-carboxylate (Ic)

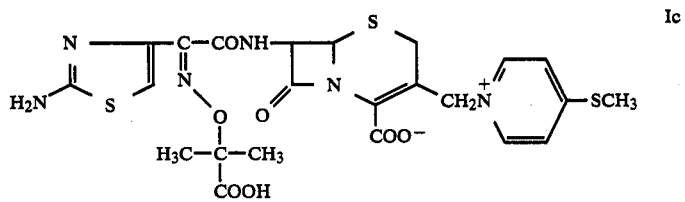

A mixture of the trifluoroacetic acid salt of 7-[(Z)-2-(2-aminothiazol-4-yl)-2-(2-carboxyprop-2-oxyimino)acetamido]cephalosporanic acid (V) (1.03 g, 1.6 mmole), sodium bicarbonate (403 mg, 4.8 mmole), potassium thiocyanate (8 g) and 4-methylthiopyridine hydroiodide (404 mg, 1.6 mmole) in water (2 ml) was adjusted to pH 7 with aqueous sodium bicarbonate and heated at 80° C. for 1 hour. The mixture was diluted with acetone (300 ml) to precipitate the product, which was collected by filtration. The crude product was fractionated by HPLC (Column: Lichrosorb RP-18, Solvent: 0.01M NH$_4$H$_2$PO$_4$ (pH 7): MeOH=85:15). The fractions containing the desired compound were collected and concentrated under reduced pressure below 30° C. The concentrate was acidified to pH 4 with dilute hydrochloric acid and chromatographed on a column of HP-20 (1.3×20 cm) and eluted with water and then with water-methanol (2:1). The fractions containing the desired product were combined, evaporated under reduced pressure and freeze-dried to give the title compound as an amorphous powder. Yield 48 mg (5%).

ir: $\nu_{max}^{KBr}$ 1780, 1670, 1625, 1535, 1380 cm$^{-1}$.

uv: $\nu_{max}^{pH7Buffer}$ 233 nm ($\epsilon$, 23000), 255 nm ($\epsilon$, 16800), 307 nm ($\epsilon$, 27700).

nmr: $\delta^{D_2O+NaHCO_3}$ ppm 1.42(6H, s, gem-CH$_3$), 2.62(3H, s, SCH$_3$), 3.15(1H, d, 18 Hz, 2-H), 3.60(1H, d, 18 Hz, 2-H), 5.15(1H, d, 4 Hz, 6-H), 5.77(1H, d, 4 Hz, 7-H), 6.90(1H, s, thiazol), 7.70(2H, d, 8 Hz, pyridine), 8.45(2H, d, 8 Hz, pyridine).

EXAMPLE 3

7-[(Z)-2-(2-Aminothiazol-4-yl)-2-(2-carboxyprop-2-oxyimino)acetamido]-3-[(2-methylthiopyridinium)methyl]-3-cephem-4-carboxylate (Ia)

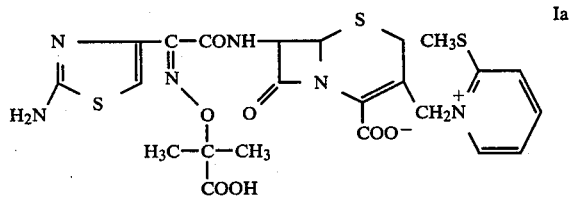

To a solution of benzhydryl 7-[(Z)-2-(2-t-butoxycarbonylprop-2-oxyimino)-2-(2-tritylaminothiazol-4-yl)acetamido]-3-iodomethyl-3-cephem-4-carboxylate (XXI) (527 mg, 0.50 mmole) and 2-methylthiopyridine (122 mg, 0.98 mmole) in nitromethane (5 ml) was added silver tetrafluoroborate (96 mg, 0.49 mmole) and the mixture was allowed to stand for 30 minutes at room temperature. The reaction mixture was diluted with ethyl acetate, washed with water, dried over Na₂SO₄ and filtered. The filtrate was evaporated in vacuo to dryness.

The residue was dissolved in wet trifluoroacetic acid (99%, 5 ml) and allowed to stand for 1 hour at room temperature. The solution was evaporated under reduced pressure below 10° C. and the residue was triturated with isopropyl ether to afford the crude product containing the title compound (210 mg). The crude product was chromatographed on a column of HP-20 resin (1.6×13 cm), eluted with 1 liter of water, 300 ml of 10% aqueous CH₃OH, 600 mg of 30% aqueous CH₃OH and 500 ml of 50% aqueous CH₃OH, successively. The 30% aqueous CH₃OH eluate containing the desired product was evaporated and the residue was subjected to further purification by HPLC (Column: Lichrosorb RP-18, Solvent: 0.01M NH₄H₂PO₄ (pH 7.2): CH₃OH=85:15). Fractions containing the product were concentrated and acidified with 1N HCl. The solution was chromatographed on a column of HP-20, which was eluted with 500 ml of water and then with 500 ml of 30% aqueous CH₃OH. Fractions containing the product were concentrated and the residue was lyophilized to give 12 mg (4%) of the title compound as an amorphous powder.

IR: $\nu_{max}^{KBr}$ cm⁻¹ 3350, 1775, 1660, 1610.
UV: $\nu_{max}^{pH\ 7\ Buffer}$ nm($\epsilon$) 247 (20500), 305 (10000).
NMR: $\nu^{D_2O}$ ppm 1.51 (6H, s), 2.84 (3H, s), 6.95 (1H, s), 8.0 (4H, m).

EXAMPLE 4

7-[(Z)-2-(2-Aminothiazol-4-yl)-2-(2-carboxyprop-2-oxyimino)acetamido]-3-[(4-ethylthiopyridinium)methyl]-3-cephem-4-carboxylate (Id)

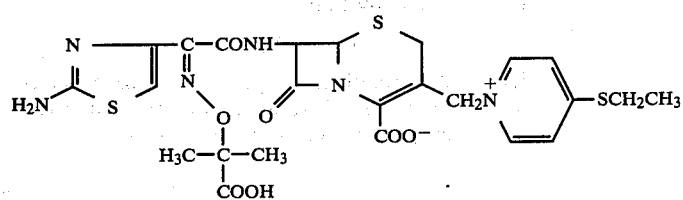

A mixture of the trifluoroacetic acid salt of 7-[(Z)-2-(2-aminothiazol-4-yl)-2-(2-carboxyprop-2-oxyimino)acetamido]cephalosporanic acid (V) (410 mg, 0.63 mmole) and 4-ethylthiopyridine (443 mg, 3.19 mmole) in water (1 ml) was adjusted to pH 7 with NaHCO₃. After the addition of potassium thiocyanate (5 g), the mixture was heated at 80° C. for 1 hour. The reaction mixture was diluted with water (20 ml) and acidified to pH 1 with 6N hydrochloric acid. The mixture was filtered and the filtrate was chromatographed on a column of HP-20 resin (1.2×20 cm) and eluted with water (1.5 liters) and then with 30% aqueous methanol. The fractions containing the desired product were combined and evaporated under reduced pressure. The aqueous residue was lyophilized to afford crude title compound (124 mg), which was purified by HPLC (Column: Lichrosorb RP-18, Solvent: 0.01M NH₄H₂PO₄ (pH 7.2):CH₃OH=80:20). The fraction containing the desired product was acidified to pH 1 with dilute hydrochloric acid and chromatographed on a column of HP-20 resin (1.2×20 cm). The column was eluted with water (1 liter) and then with 30% aqueous methanol. The methanolic fraction containing the desired product was concentrated under reduced pressure and the aqueous concentrate was lyophilized to give the title compound as an amorphous powder. Yield 27 mg (7%).

IR: $\nu_{max}^{KBr}$ cm⁻¹ 1775, 1670, 1625, 1540, 1360.
UV: $\nu_{max}^{pH\ 7\ Buffer}$ nm($\epsilon$) 234 (21900), 255 (sh) (16300), 308 (23300).
NMR: $\delta^{D_2O+NaHCO_3}$ ppm 1.40 (3H, t, 6 Hz, Et), 1.48 (6H, s, Me), 5.80 (1H, d, 4 Hz, 7-H), 6.93 (1H, s, thiazole-H), 7.75 (2H, d, 8 Hz, pyridine-H), 8.48 (2H, d, 8 Hz, pyridine-H).

EXAMPLE 5

7-[(Z)-2-(2-Aminothiazol-4-yl)-2-(2-carboxyprop-2-oxyimino)acetamido]-3-[(4-isopropylthiopyridinium)methyl]-3-cephem-4-carboxylate (Ie)

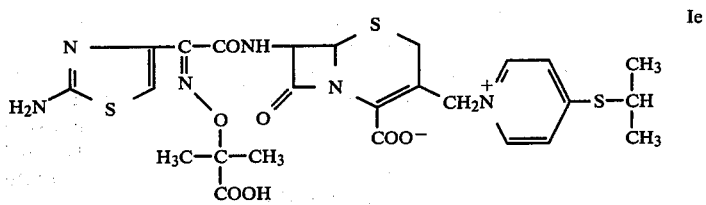

Silver tetrafluoroborate (100 mg, 0.52 mmole) was added to a mixture of benzhydryl 7-[(Z)-2-(2-t-butoxycarbonylprop-2-oxyimino)-2-(2-tritylaminothiazol-4-yl)acetamido]-3-iodomethyl-3-cephem-4-carboxylate (XXI) (530 mg, 0.5 mmole) and 4-isopropylthiopyridine (153 mg, 1 mmole) in methylene chloride (5 ml). After stirring for 1 hour at room temperature, the mixture was diluted with ethyl acetate (100 ml), washed with water, dried and filtered. The filtrate was evaporated under reduced pressure. The residue was triturated with ether (100 ml) and filtered to give the quaternary compound (300 mg), which was deblocked with wet trifluoroacetic acid (TFA) (99%) (2 ml) for 1 hour at room temperature. The mixture was diluted with ether and filtered to give the crude TFA salt of the title compound (170 mg). This was purified by HPLC (Lichrosorb RP-18, 5% methanol). The fraction containing the desired product was acidified to pH 1 with dilute hydrochloric acid and chromatographed on a column of HP-20 resin (1.9×10 cm). The column was eluted with water and then with 30% aqueous methanol. The methanolic fraction containing the desired product was concentrated under reduced pressure and then lyophilized to give the product as an amorphous powder. Yield 16 mg (2.5%).

IR: $\nu_{max}^{KBr}$ cm$^{-1}$ 3600–3000, 1780, 1660, 1625, 1540, 1360, 1160, 1110.

UV: $\nu_{max}^{pH 7\ Buffer}$ nm($\epsilon$) 234 (23300), 255 (16700), 310 (27600).

NMR: $\delta^{D_2O+NaHCO_3}$ ppm 1.4–1.5 (12H, m), 6.91 (1H, s, thiazole-H), 7.70 (2H, d, 7 Hz, pyridine-H), 8.47 (2H, d, 7 Hz, pyridine-H).

EXAMPLE 6

7-[(Z)-2-(2-Aminothiazol-4-yl)-2-(2-carboxyprop-2-oxyimino)acetamido]-3-[(4-methylthiopyridinium)methyl]-3-cephem-4-carboxylate (Ic)

A. Benzyhydryl 3-Chloromethyl-7-phenylacetamido-3-cephem-4-carboxylate (VII)

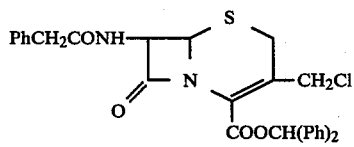

Pyridine (1.6 g, 20 mmole) was added to a slurry of PCl$_5$ (4.2 g, 20 mmole) in CH$_2$Cl$_2$ (100 ml) and the mixture was stirred at 20° C. for 20 minutes and then cooled to −40° C. To the mixture was added benzhydryl 3-hydroxymethyl-7-phenylacetamido-3-cephem-4-carboxylate (VI) (5.1 g, 10 mmole) in one portion. The mixture was stirred at −10° C. for 30 minutes. The solution was washed with ice water (20 ml) and poured into ice saturated aqueous NaHCO$_3$ (100 ml), with stirring. The CH$_2$Cl$_2$ layer was washed successively with saturated aqueous NaCl (50 ml), 10% HCl (50 ml) and saturated aqueous NaCl. The dried CH$_2$Cl$_2$ solution was evaporated and the residue triturated with n-hexane to give 5.2 g (98%) of VII. Mp. 85° C. (dec.).

ir: $\nu_{KBr}$ 3250, 1780, 1720, 1660 cm$^{-1}$.

uv: $\nu_{EtOH}^{max}$ 265 nm (E$_{1cm}$1% 140).

nmr: $\delta_{ppm}^{DMSO-d6}$ ppm 3.53 (2H, s), 3.62 (2H, broad s), 4.39 (2H, s), 5.13 (2H, d, J=4.5), 5.75 (1H, d-d, J=4.5, 9), 6.93 (1H, s), 7.1~7.6 (15H, m), 9.12 (1H, d, J=9).

Analysis Calc'd. for C$_{29}$H$_{25}$N$_2$O$_4$SCl.½H$_2$O: C, 64.26; H, 4.83; N, 5.17; S, 5.92. Found: C, 64.53; H, 5.15; N, 4.78; S, 5.92.

B. Benzhydryl 3-Chloromethyl-7-phenylacetamido-3-cephem-4-carboxylate 1-Oxide (VIII)

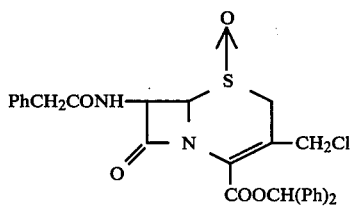

A mixture of VII (1.5 g, 2.8 mmole) and 3-chloroperbenzoic acid (970 mg. 5.6 mmole) in CH$_3$OH:CH$_2$Cl$_2$ (3:7) (50 ml) was stirred for 3 hours at room temperature and then evaporated to dryness. The residue was triturated with ether (50 ml) to separate 1.1 g (71%) of VIII as a colorless amorphous powder. Mp. 196° C.~199° C. (dec.).

ir: $\nu_{KBr}$ 3300, 1780, 1660, 1620, 1030 cm$^{-1}$.

uv: $\lambda_{max}^{EtOH}$ 272 nm (E$_{1cm}$1% ca. 140).

nmr: $\delta^{DMSO-d6}$ ppm 3.69 and 3.71 (2H, each s), 3.68 and 3.99 (each 1H, d, J=15), 4.38 and 4.62 (each 1H, d, J=12), 4.96 (1H, d, J=4.5), 5.85 (1H, d-d, J=4.5, 7.5), 6.90 (1H, s), 7.1~7.5 (15H, m), 8.40 (1H, d, J=7.5).

Analysis Calc'd. for C$_{29}$H$_{25}$N$_2$O$_5$SCl: C, 63.44; H, 4.59; N, 5.10; S, 5.84. Found: C, 63.35; H, 4.51; N, 4.81; S, 6.02.

C. Benzhydryl 3-Iodomethyl-7-phenylacetamido-3-cephem-4-carboxylate 1-Oxide (IX)

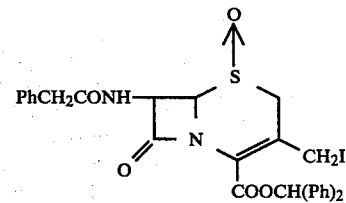

A mixture of VIII (1 g, 1.8 mmole) and NaI (810 mg, 5.4 mmole) in acetone (10 ml) was stirred for 3 hours at ambient temperature and then evaporated in vacuo. The residual oil was partitioned between 10% CH$_3$OH in CH$_2$Cl$_2$ (50 ml) and water (10 ml). The organic solvent layer was washed with 10% w/v aqueous sodium thiosulfate (10 ml) and saturated aqueous NaCl, dried over MgSO$_4$ and then evaporated to dryness to give 1.1 g (94%) of IX melting at 144° C. (dec.).

ir: $\nu_{KBr}$ 3300, 1790, 1710, 1650, 1030 cm$^{-1}$.

uv: $\lambda_{max}^{EtOH}$ 291 nm (E$_{1\ cm}$1% ca. 140).

nmr: $\delta^{DMSO-d6}$ ppm 3.58 and 3.60 (2H, each s), 3.84 (2H, broad s), 4.25 and 4.99 (each 1H, d, J=9), 4.90 (1H, d, J=4.5), 5.80 (1H, d-d, J=4.5 and 7.5), 6.91 (1H, s), 7.1~7.6 (15H, m), 8.35 (1H, d).

D. Benzhydryl 3-[(4-Methylthiopyridinium)methyl]-7-phenylacetamido-3-cephem-4-carboxylate 1-Oxide Iodide (X)

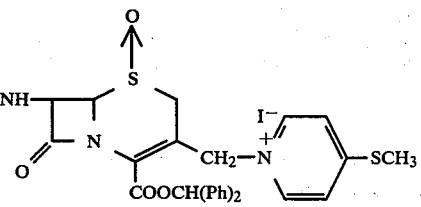

A mixture of IX (1 g, 1.6 mmole) and 4-methylthiopyridine (390 mg, 3.1 mmole) in tetrahydrofuran (15 ml) was stirred for 30 minutes at ambient temperature, and then evaporated to dryness under reduced pressure. The residue was triturated with ether to give 1.2 g (97%) of X, melting at 133° C. (dec.).

ir: $\nu_{KBr}$ 3400, 1800, 1720, 1680, 1620, 1030 cm$^{-1}$.

uv: $\lambda_{max}^{EtOH}$ 267 nm (E$_{1\ cm}$1% 130), 309 nm (E$_{1\ cm}$1% 320).

nmr: $\delta^{DMSO-d6}$ ppm 2.69 (3H, s), 3.60 (2H, s), ca. 3.7 (2H, m), 5.00 (1H, d, J=4.5), 3.35 (2H, s), 5.98 (1H, d-d, J=4.5 and 7.5), 6.90 (1H, s), 7.1~7.5 (15H, m), 7.86 and 8.50 (each 2H, d, J=6), 8.9 (1H, d, J=7.5).

Analysis Calc'd. for $C_{35}H_{32}N_3O_5S_2I$: C, 54.90; H, 4.21; N, 5.49; S, 8.37. Found: C, 54.70; H, 3.90; N, 5.20; S, 8.59.

E. Benzhydryl 7-Amino-3-[(4-methylthiopyridinium)methyl]-3-cephem-4-carboxylate 1-Oxide Iodide (XI)

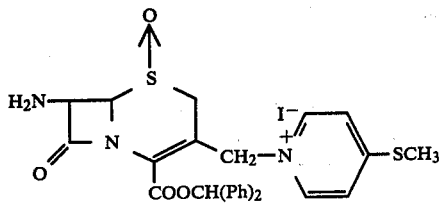

XI

To a slurry of $PCl_5$ (813 mg, 3.9 mmole) in $CH_2Cl_2$ (10 ml) was added pyridine (308 mg, 3.9 mmole) and the mixture was stirred for 20 minutes and then cooled to $-40°$ C. To the mixture was added X (1 g, 1.3 mmoles) in one portion. The mixture was stirred at $-10°$ C. to $-15°$ C. for 3 hours and then cooled to $-30°$ C. To the cold solution was added $CH_3OH$ (1 ml) and the mixture was warmed to room temperature and stirred for 30 minutes at room temperature. To the solution was added ice-water (10 ml) and the separated oil was extracted with $CH_3OH:CH_2Cl_2$ (3:7). The combined extracts were washed with saturated aqueous NaCl (10 ml), dried over $MgSO_4$ and evaporated to dryness to give 3 g of an oil. The oil was triturated with ether (4×10 ml) to yield 1.1 g (100%) of XI as an amorphous powder melting at 132° C. (dec.), which showed a single spot in TLC (Rf. 0.6, solv. $CHCl_3/MeOH=4/1$).

ir: $\nu_{KBr}$ 3400, 2600, 1790, 1720, 1625, 1040 cm$^{-1}$.
uv: $\lambda_{max}^{EtOH}$ 264 nm ($E_{1\ cm}^{1\%}$ 97), 310 nm ($E_{1\ cm}^{1\%}$ 270).
nmr: $\delta^{DMSO-d6+D2O}$ ppm 2.69 (3H, s), 5.29 (2H, s), 5.45 (2H, broad s), 6.86 (1H, s), 7.1~7.5 (10H, m), 7.85 and 8.60 (each 2H, d, J=6).

F. Benzhydryl 7-[(Z)-2-(2-t-Butoxycarbonylprop-2-oxyimino)-2-(2-tritylaminothiazol-4-yl)acetamido]-3-[(4-methylthiopyridinium)methyl]-3-cephem-4-carboxylate 1-Oxide Iodide (XII)

To a suspension of (Z)-2-(2-t-butoxycarbonylprop-2-oxyimino)-2-(2-tritylaminothiazol-4-yl)acetic acid (540 mg, 1 mmole) in $CH_2Cl_2$ (10 ml) was added $PCl_5$ (208.5 mg, 1 mmole) at $-10°$ C. with stirring. The mixture was stirred for 20 minutes at $-5°$ C. and added at $-20°$ C. to a solution of XI (632 mg, 1 mmole) in $CH_2Cl_2$ (10 ml) containing N,O-bistrimethylsilylacetamide (0.8 ml, 3 mmole). The mixture was stirred at room temperature for 3 hours and then diluted with ice-water (10 ml). The organic layer was washed with water (10 ml), dried over $MgSO_4$ and evaporated to dryness. The residual oil was triturated with ether (10 ml) to give 740 mg (86% overall yield from X) of the product showing two spots at Rf. 0.6 and Rf. 0.7 in TLC (solv. $CHCl_3:CH_3OH=10:1$), which were identical with those of XII and XIII, respectively, prepared in Example 8. This indicates that the starting material XI of this reaction (Step F) also contained some XVI (having an Rf. value essentially the same as that of XI), since reduction of the sulfoxide moiety would be more likely to occur during the conversion of X to XI (Step E) than during the conversion of XI to XII (Step F). Mp. 146° C. (dec.).

ir: $\nu_{KBr}$ 3400, 1790, 1690, 1620, 1010 cm$^{-1}$.
uv: $\nu_{max}^{EtOH}$ 235 nm ($E_{1\ cm}^{1\%}$ 260), 260 nm ($E_{1\ cm}^{1\%}$ 180), 309 nm ($E_{1\ cm}^{1\%}$ 240).

G. Benzhydryl 7-[(Z)-2-(2-t-Butoxycarbonylprop-2-oxyimino)-2-(2-tritylaminothiazol-4-yl)acetamido]-3-[(4-methylthiopyridinium)methyl]-3-cephem-4-carboxylate Iodide (XIII)

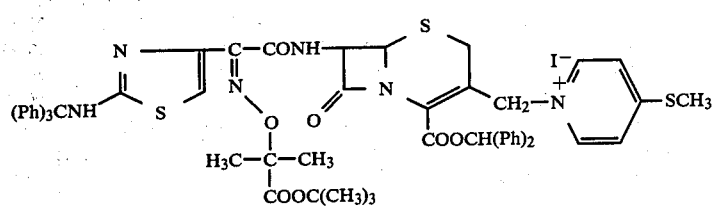

XIII

To a cold solution ($-10°$ C.) of XII (600 mg, ca. 0.5 mmole) in dry acetone (10 ml) was added KI (332 mg, 2 mmole) followed by acetyl chloride (78.5 mg, 1 mmole). After stirring for 20 minutes at $-10°$ C., KI (332 mg) and acetyl chloride (78.5 mg) were added again. After stirring for another 20 minutes at $-10°$ C., a solution of sodium metabisulfite (4% w/v, 6 ml) was added, while maintaining the temperature at 0° C. The solution was then extracted twice with $CH_2Cl_2$ (2×20 ml). The combined extracts were washed with water (10 ml), dried over $MgSO_4$ and evaporated to give XIII as a reddish powder, melting at 125° C. (dec.). Yield 570 mg (Quantitative).

ir: $\nu_{KBr}$ 3400, 1720, 1690, 1620 cm$^{-1}$.

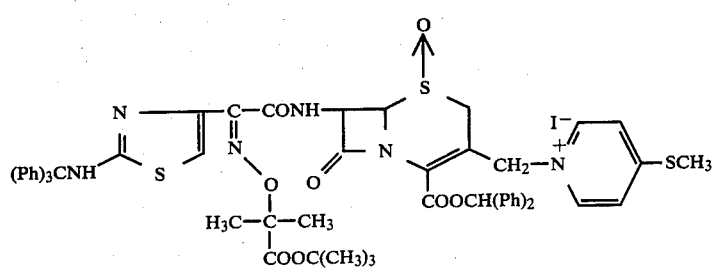

XII uv: $\lambda_{max}^{EtOH}$ 260 nm ($E_1\ _{cm}^{1\%}$ 170), 310 nm ($E_1\ _{cm}^{1\%}$ 220).

Analysis Calc'd. for $C_{59}H_{57}N_6O_7S_3I\cdot 3H_2O$: C, 57.18; H, 5.12; N, 6.78; S, 7.76. Found: C, 56.87; H, 4.59; N, 6.23; S, 8.55.

H. 7-[(Z)-2-(2-Aminothiazol-4-yl)-2-(2-carboxyprop-2-oxyimino)acetamido]-3-[(4-methylthiopyridinium)methyl]-3-cephem-4-carboxylate (Ic)

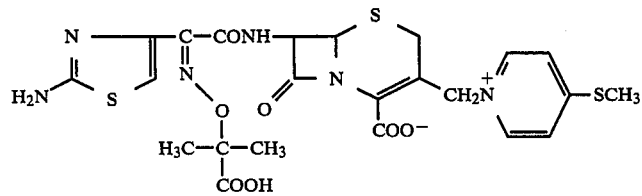

A mixture of XIII (500 mg, 0.43 mmole) and trifluoroacetic acid (4 ml) was stirred for 1 hour at room temperature. To the mixrture was added ether (20 ml) to precipitate 302 mg of crude Ic as the TFA salt. The TFA salt (100 mg) was purified by HPLC (Column, Lichrosorb RP-18, 4 mm×30 cm; Mobile phase, 0.01M phosphate buffer/$CH_3OH$=87.5/12.5). The fraction containing Ic was evaporated to dryness. The residue was dissolved in 5% HCl (5 ml) and chromatographed on an HP-20 column (30 ml) using water, 30% $CH_3OH$ and 50% $CH_3OH$ successively. Fractions containing the desalted product were concentrated in vacuo to a small volume and lyophilized to give 37 mg of Ic (yield 44%). Mp. >150° C. (gradual dec.).

ir: $\nu_{KBr}$ 3400, 1770, 1660, 1620, 1530 cm$^{-1}$.

uv: $\lambda_{max}^{EtOH}$ 233 nm ($E_1\ _{cm}^{1\%}$ 350), 255 nm ($E_1\ _{cm}^{1\%}$ 250), 307 nm ($E_1\ _{cm}^{1\%}$ 400).

EXAMPLE 7

Alternate Route for the Synthesis of Compound XIII in the Preparation of 7-[(Z)-2-(2-Aminothiazol-4-yl)-2-(2-carboxyprop-2-oxyimino)acetamido]-3-[(4-methylthiopyridinium)methyl]-3-cephem-4-carboxylate (Ic)

A. Benzhydryl 3-Iodomethyl-7-phenylacetamido-3-cephem-4-carboxylate (XIV)

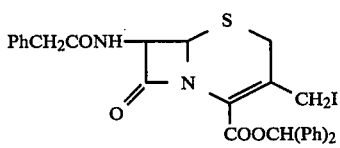

A solution of Compound VII from Example 6, Step A (1.07 g, 2 mmoles) in acetone (10 ml) containing NaI (900 mg, 6 mmoles) was stirred for 2 hours at ambient temperature. The reaction mixture was evaporated under reduced pressure and the residue was partitioned between $CH_2Cl_2$ (30 ml) and water (10 ml). The lower layer was washed with 10% w/v aqueous sodium thiosulfate (10 ml) and saturated aqueous NaCl (10 ml), dried over $MgSO_4$ and evaporated to dryness to give 1.1 g (88%) of XIV as a reddish amorphous powder melting at 75° C. (dec.).

ir: $\nu_{KBr}$ 3300, 1780, 1720, 1660 cm$^{-1}$.

uv: $\lambda_{max}^{EtOH}$ 280 nm ($E_1\ _{cm}^{1\%}$ 100).

B. Benzhydryl 3-[(4-Methylthiopyridinium)methyl]-7-phenylacetamido-3-cephem-4-carboxylate Iodide (XV)

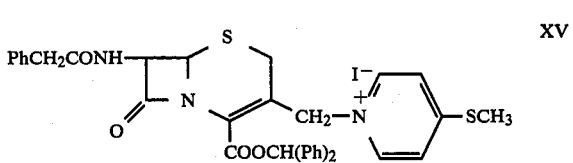

A mixture of XIV (900 mg, 1.4 mmoles) and 4-methylthiopyridine (360 mg, 2.9 mmoles) in $CH_2Cl_2$ (10 ml) was stirred at room temperature for 2 hours. The mixture was evaporated to dryness and diluted with ether (10 ml) to afford a precipitate, which was collected by filtration and dried to give 1 g (95%) of XV, melting at 104° C.

ir: $\nu_{KBr}$ 3200, 1780, 1730, 1660, 1620 cm$^{-1}$.

uv: $\lambda_{max}^{EtOH}$ 260 nm ($E_1\ _{cm}^{1\%}$ 190), 309 nm ($E_1\ _{cm}^{1\%}$ 200).

C. Benzhydryl 7-Amino-3-[(4-methylthiopyridinium)methyl]-3-cephem-4-carboxylate Iodide (XVI)

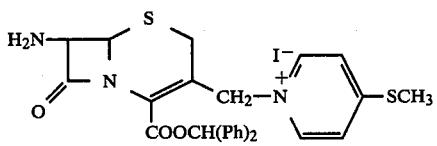

To a suspension of $PCl_5$ (750 mg, 3.6 mmoles) in $CH_2Cl_2$ (10 ml) was added pyridine (284 mg, 3.6 mmoles) in $CH_2Cl_2$ (3 ml) and the mixture was stirred for 20 minutes and then cooled to −40° C. To the mixture was added XV (900 mg, 1.2 mmole) and the mixture was stirred for 6 hours at −10° C. to −15° C. and then cooled to −40° C. To the cold solution was added $CH_3OH$ (1 ml) and the mixture was warmed to room temperature and stirred for 1 hour. Ice-water (10 ml) was added and the separated oily precipitate was dissolved in $CH_3OH$:$CH_2Cl_2$ (3:7). The solution was washed with saturated aqueous NaCl, dried over $MgSO_4$ and evaporated to dryness. The residual oil was triturated with ether (2×10 ml) to give XVI as a reddish amorphous powder. Yield 390 mg (51%). Mp. 145° C. (dec.).

ir: $\nu_{KBr}$ 3400, 1780, 1720, 1625 cm$^{-1}$.

uv: $\lambda_{max}^{EtOH}$ 257 nm ($E_1\ _{cm}^{1\%}$ 130), 309 nm ($E_1\ _{cm}^{1\%}$ 210).

D. Benzhydryl 7-[(Z)-2-(2-t-Butoxycarbonylprop-2-oxyimino)-2-(2-tritylaminothiazol-4-yl)acetamido]-3-[(4-methylthiopyridinium)methyl]-3-cephem-4-carboxylate Iodide (XIII)

To a suspension of (Z)-2-(t-butoxycarbonylprop-2-oxyimino)-2-(2-tritylaminothiazol-4-yl)acetic acid in $CH_2Cl_2$ (5 ml) was added $PCl_5$ (104 mg, 0.5 mmole) at $-10°$ C. with stirring. After stirring for 20 minutes at $-5°$ C., the mixture was added at $-20°$ C. to a solution of trimethylsilylated XVI [316 mg (0.5 mmole) of XVI and 0.37 ml (1.5 mmoles) of N, O-bis(trimethylsilyl)acetamide in $CH_2Cl_2$ (5 ml)]. The mixture was stirred at room temperature for 2 hours and added to ice-water (5 ml). The solvent was washed with water (5 ml), dried over $MgSO_4$ and evaporated to dryness to give 530 mg (93%) of XIII as a reddish amorphous powder, which showed the same Rf. value as the XIII prepared from XII in Example 6, Step G. TLC [silica gel, eluted with $CH_3OH:CHCl_3$ (1:10) and developed in an iodine chamber]: Rf. 0.7.

EXAMPLE 8

Alternate Route for the Synthesis of Compound XIII in the Preparation of 7-[(Z)-2-(2-Aminothiazol-4-yl)-2-(2-carboxyprop-2-oxyimino)acetamido]-3-[(4-methylthiopyridinium)methyl]-3-cephem-4-carboxylate (Ic)

A. Benzhydryl 7-Amino-3-chloromethyl-3-cephem-4-carboxylate (XVII)

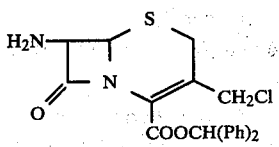

To a slurry of $PCl_5$ (8.3 g, 40 mmoles) in $CH_2Cl_2$ (100 ml) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate (VI) (5.1 g, 10 mmoles) with stirring at $-40°$ C., in one portion. The mixture was stirred at $-10°$ C. for 15 minutes and allowed to stand at $-10°$ C. to $-15°$ C. for 7 hours. To the cooled solution ($-20°$ C.) was added propane-1,3-diol (10 ml) and the mixture was allowed to stand at $-20°$ C. for 16 hours and then at room temperature for 20 minutes with stirring. The resulting solution was washed with ice-water ($2\times20$ ml) and saturated aqueous NaCl (10 ml), dried over $MgSO_4$ and concentrated in vacuo. The gummy residue (12 g) was dissolved in a mixture of $CHCl_3$ and n-hexane (2:1), and subjected to chromatography using a silica gel column (200 g) and the same solvent as eluant. Fractions containing the title compound were evaporated in vacuo and the residue triturated with n-hexane to give XVII (2:1 g, 51%), melting at $>110°$ C. (dec.).

ir: $\nu_{KBr}$ 3400, 2800, 1785, 1725 $cm^{-1}$.
uv: $\lambda_{max}^{EtOH}$ 265 nm ($E_1\ _{cm}^{1\%}$ 160).
nmr: $\delta^{DMSO-d6+CDCl_3}$ ppm 3.69 (2H, s), 4.43 (2H, s), 5.09 (1H, d, J=4.5 Hz), 5.24 (1H, d, J=4.5 Hz), 6.87 (1H, s), 7.3 (10H, m).

B. Benzhydryl 7-[(Z)-2-(2-t-Butoxycarbonylprop-2-oxyimino)-2-(2-tritylaminothiazol-4-yl)acetamido]-3-chloromethyl-3-cephem-4-carboxylate (XVIII)

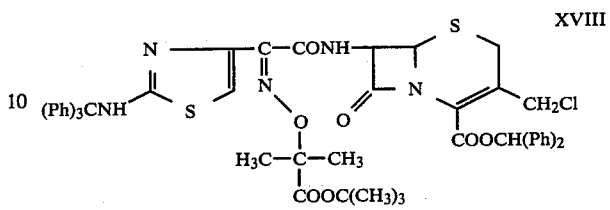

A mixture of (Z)-2-(2-t-butoxycarbonylprop-2-oxyimino)-2-(2-tritylaminothiazol-4-yl)acetic acid (1.94 g, 3.6 mmoles), dicyclohexylcarbodiimide (742 mg, 3.6 mmoles) and N-hydroxybenztriazole (486 mg, 3.6 mmoles) in tetrahydrofuran (45 ml) was stirred at room temperature for 45 minutes, during which time dicyclohexylurea was precipitated. The precipitate was removed by filtration and the filtrate was mixed with XVII (1.5 g, 3.6 mmoles), stirred overnight at room temperature and evaporated in vacuo. The residual oil was dissolved in $CHCl_3$ (20 ml), washed with saturated aqueous $NaHCO_3$ and saturated aqueous NaCl, dried over $MgSO_4$ and evaporated to dryness. The residue (3.9 g) was dissolved in n-hexane:$CHCl_3$ (1:2) and passed through a silica gel column (40 g), using the same solvent as eluant. Fractions containing the title compound were evaporated in vacuo to give 1.3 g (39%) of XVIII, melting at $>100°$ C. (dec.).

ir: $\nu_{KBr}$ 3390, 1790, 1715, 1690 $cm^{-1}$.
uv: $\lambda_{max}^{EtOH}$ 240 nm ($E_1\ _{cm}^{1\%}$ 280), 265 nm ($E_1\ _{cm}^{1\%}$ 190).
nmr: $\delta^{CDCl_3}$ ppm 1.45 (9H, s), 1.63 and 1.66 (6H, each s), 3.49 (2H, broad s), 4.34 (2H, s), 4.96 (1H, d, J=4.5 Hz), 5.90 (1H, d-d, J=4.5 and 7.5), 6.66 (1H, s), 6.86 (1H, s), 7.0~7.5 (25H, m), 8.23 (1H, d, J=7.5 Hz).

C. Benzhydryl 7-[(Z)-2-(2-t-Butoxycarbonylprop-2-oxyimino)-2-(2-tritylaminothiazol-4-yl)acetamido]-3-chloromethyl-3-cephem-4-carboxylate 1-Oxide (XIX)

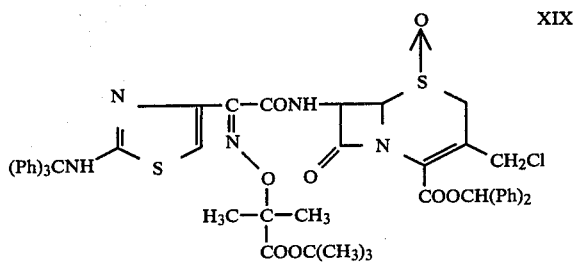

A mixture of XVIII (0.5 g, 0.53 mmole) and 3-chloroperbenzoic acid (190 mg, 1.1 mmoles) in $CH_2Cl_2$ (5 ml) was stirred for 2 hours at room temperature. The reaction mixture was diluted with $CH_2Cl_2$ (10 ml), washed with saturated aqueous $NaHCO_3$ (5 ml) and saturated aqueous NaCl, dried over $MgSO_4$ and evaporated to dryness in vacuo to give 504 mg (99%) of XIX as an amorphous powder melting at 91° C.

ir: $\nu_{KBr}$ 3350, 1805, 1730, 1690, 1030 $cm^{-1}$.
uv: $\lambda_{max}^{EtOH}$ 260 nm ($E_1\ _{cm}^{1\%}$ 200).

D. Benzhydryl 7-[(Z)-2-(2-t-Butoxycarbonylprop-2-oxyimino)-2-(2-tritylaminothiazol-4-yl)acetamido]-3-iodomethyl-3-cephem-4-carboxylate 1-Oxide (XX)

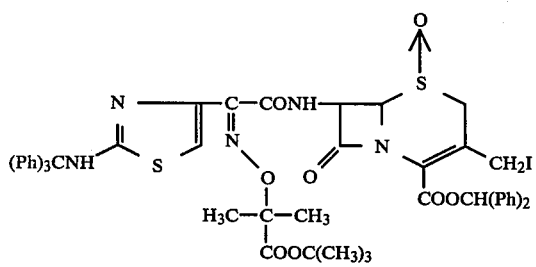

A mixture of XIX (410 mg., 0.43 mmole) and NaI (193 mg, 1.3 mmole) in acetone (5 ml) was stirred for 2 hours at room temperature and evaporated in vacuo. To the residue was added a mixture of $CH_2Cl_2$ (20 ml) and $H_2O$ (5 ml). The organic layer was washed with 10% w/v sodium thiosulfate (5 ml) and aqueous NaCl. After drying, the solution was evaporated in vacuo to give 450 mg (100%) of XX as an amorphous powder melting at 110° C. (dec.).

ir: $\nu_{KBr}$ 3350, 1800, 1725, 1690, 1030 cm$^{-1}$.

uv: $\lambda_{max}{}^{EtOH}$ 260 nm ($E_{1\,cm}{}^{1\%}$ 180).

E. Benzhydryl 7-[(Z)-2-(2-t-Butoxycarbonylprop-2-oxyimino)-2-(2-tritylaminothiazol-4-yl)acetamido]-3-[(4-methylthiopyridinium)methyl]-3-cephem-4-carboxylate 1-Oxide Iodide (XII)

A mixture of XX (370 mg, 0.35 mmole) and 4-methylthiopyridine (88 mg, 0.7 mmole) in $CH_2Cl_2$ (5 ml) was stirred overnight at room temperature. The reaction mixture was evaporated to dryness in vacuo. To the residue was added ether (20 ml) to give a precipitate, which was collected by filtration, washed with ether and dried to give 270 mg (65%) of XII melting at >150° C. (dec.). This product showed a single spot at Rf. 0.6 in TLC (solvent: $CHCl_3:CH_3OH=10:1$).

ir: $\nu_{KBr}$ 3400, 1800, 1725, 1685, 1625, 1030 cm$^{-1}$.

uv: $\lambda_{max}{}^{EtOH}$ 260 nm ($E_{1\,cm}{}^{1\%}$ 210), 308 nm ($E_{1\,cm}{}^{1\%}$ 190).

F. Benzhydryl 7-[(Z)-2-(2-t-Butoxycarbonylprop-2-oxyimino)-2-(2-tritylaminothiazol-4-yl)acetamido]-3-[(4-methylthiopyridinium)methyl]-3-cephem-4-carboxylate Iodide (XIII)

To a solution of XII (220 mg, 0.19 mmole) in dry acetone (3 ml) was added KI (126 mg, 0.76 mmole) followed by acetyl chloride (30 mg, 0.38 mmole) at −10° C. with stirring. After stirring for 20 minutes at −10° C., additional amounts of KI (126 mg) and acetyl chloride (30 mg) were added. After stirring for another 20 minutes at −10° C., an aqueous solution of sodium metabisulfite (3 ml, 4 g/100 ml) was added while maintaining the temperature at 0° C. The mixture was extracted twice with $CH_2Cl_2$ (2×15 ml). The combined extracts were washed with NaCl, dried over $MgSO_4$ and concentrated to dryness to give 215 mg (99%) of XIII as a reddish amorphous powder, which showed a single spot at Rf. 0.7 in TLC (solvent: $CH_3Cl_3:CH_3OH=10:1$; detection, $I_2$).

EXAMPLE 9
Alternate Route for the Synthesis of Compound XIII in the Preparation of 7-[(Z)-2-(2-Aminothiazol-4-yl)-2-(2-carboxyprop-2-oxyimino)acetamido]-3-[(4-methylthiopyridinium)methyl]-3-cephem-4-carboxylate (Ic)

A. Benzhydryl 7-[(Z)-2-(2-t-Butoxycarbonylprop-2-oxyimino)-2-(2-tritylaminothiazol-4-yl)acetamido]-3-iodomethyl-3-cephem-4-carboxylate (XXI)

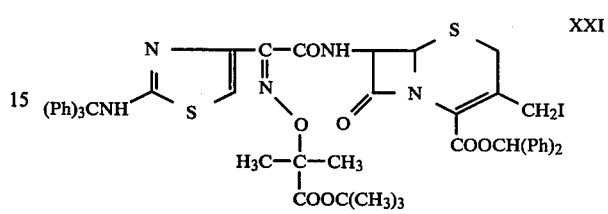

A mixture of XVIII (from Example 8, Step B) (500 mg, 0.53 mmole) and NaI (240 mg, 1.6 mmoles) in acetone (3 ml) was stirred for 2 hours at room temperature and evaporated in vacuo. To the residue were added $CH_2Cl_2$ (20 ml) and water (10 ml). The organic layer was washed with 10% w/v aqueous sodium thiosulfate (5 ml) and aqueous NaCl (5 ml), dried over $MgSO_4$ and evaporated to dryness to give 540 mg (99%) of XXI as an amorphous powder melting at 106° C. (dec.).

ir: $\nu_{KBr}$ 3350, 1790, 1690 cm$^{-1}$.

uv: $\lambda_{max}{}^{EtOH}$ 240 nm ($E_{1\,cm}{}^{1\%}$ 270), 265 nm ($E_{1\,cm}{}^{1\%}$ 190).

nmr: $\delta^{CDCl_3}$ ppm 1.44 (9H, s), 1.65 (6H, s), 3.50 and 3.58 (each 1H, s), 4.28 (2H, s), 4.98 (1H, d, J=4.5 Hz), 5.85 (1H, d-d, J=4.5 and 7.5 Hz), 6.70 (1H, s), 6.90 (1H, s), 7.1~7.5 (25H, m).

B. Benzhydryl 7-[(Z)-2-(2-t-butoxycarbonylprop-2-oxyimino)-2-(2-tritylaminothiazol-4-yl)acetamido]-3-[(4-methylthiopyridinium)methyl]-3-cephem-4-carboxylate Iodide (XIII)

A mixture of XXI (400 mg, 0.39 mmole) and 4-methylthiopyridine (98 mg, 0.77 mmole) in $CH_2Cl_2$ (5 ml) was stirred for 7 hours, and evaporated in vacuo. The residue was triturated with ether (2×10 ml) to give 270 mg (60%) of XIII as a reddish amorphous powder. The Rf. value of this product was the same as that of the product obtained in Example 8, Step F. TLC: silica gel plate, eluted with $CH_3OH:CHCl_3$ (1.10) and developed in an iodine chamber. Rf. 0.7.

We claim:
1. A compound of the formula

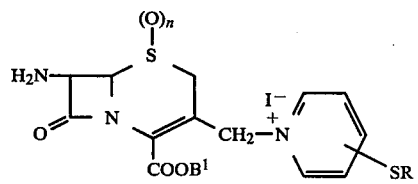

wherein R is methyl, ethyl or isopropyl, n is zero or one, and $B^1$ is hydrogen or a carboxyl-protecting group, or a salt thereof.

2. A compound of claim 1 wherein R is methyl and $B^1$ is benzhydryl, or a salt thereof.

3. The compound of claim 2 which is benzhydryl 7-amino-3-[(4-methylthiopyridinium)methyl]-3-cephem-4-carboxylate 1-oxide iodide.

4. The compound of claim 2 which is benzhydryl 7-amino-3-[(4-methylthiopyridinium)methyl]-3-cephem-4-carboxylate iodide.

* * * * *